United States Patent [19]

Nafissi-Varchei

[11] 4,021,570

[45] May 3, 1977

[54] TREATMENT OF OXYURIASIS

[75] Inventor: Mohammad Mehdi Nafissi-Varchei, North Caldwell, N.J.

[73] Assignee: Schering Corporation, Kenilworth, N.J.

[22] Filed: Apr. 20, 1976

[21] Appl. No.: 678,776

[52] U.S. Cl. .............................................. 424/300
[51] Int. Cl.$^2$ ........................................ A61K 31/27
[58] Field of Search ................................... 424/300

[56] References Cited

UNITED STATES PATENTS 3,865,948   2/1975   Eichler et al. ................... 424/300

FOREIGN PATENTS OR APPLICATIONS 7,008,706   10/1971   South Africa ................... 424/308
7,400,660   9/1974    South Africa ................... 424/308

Primary Examiner—Jerome D. Goldberg
Attorney, Agent, or Firm—Bruce M. Eisen; Stephen B. Coan

[57] ABSTRACT

A novel compound, N-carbomethoxy-N'-methyl-N'-(2-nitro-4-N-propyloxyphenyl)thiourea, is highly effective in the treatment of pinworm infections.

1 Claim, No Drawings

TREATMENT OF OXYURIASIS

This invention relates to the efficient treatment of oxyuriasis (pinworm infection) in man and other susceptible animal species by means of the administration of the novel chemical compound N-carbomethoxy-N'-methyl-N'-(2-nitro-4-n-propyloxyphenyl)thiourea.

Oxyurides or pinworms are troublesome parasitic helminths which commonly infest the intestinal tract of man and other animals. In man, the infection is found in all economic classes and is common in the temperate climates and is especially prevalent among school children.

It has now been found that the administration of N-carbomethoxy-N'-methyl-N'-(2-nitro-4-n-propyloxyphenyl)thiourea is highly effective in curing oxyuriasis. In particular, it is considerably more effective than pyrantal pamoate (Antiminth), the current drug of choice for treating pinworm infections.

Other substituted phenyl thioureas have been taught in the literature to be useful in the treatment of various helminth infections. See for example U.S. Pat. No. 3,865,948, South African Patent 7,400,660 and South African Patent 7,008,706. The subject thiourea is novel and outside the scope of the compounds described therein. The compound of this invention has been found to be more effective in treating oxyuriasis than representative compounds of the foregoing patents.

N-carbomethoxy-N'-methyl-N'-(2-nitro-4-n-propyloxyphenyl)thiourea can be prepared (as exemplified immediately below) by the methylation of the corresponding unsubstituted thiourea. The latter can be prepared in standard manner by the reaction of carbomethoxyisothiocyanate with the corresponding aniline analogous to the procedures in the above cited patents.

EXAMPLE

A suspension of 108 mg sodium hydride in 10 ml dry benzene is added portionwise to a stirring solution of 1.409 g 1-carbomethoxy-3-(2'-nitro-4'-propyloxyphenyl)thiourea in 100 ml of dry benzene at 0° C. After 30 minutes 635 mg methyl iodide is added to this mixture and heated at 70° C for 3 hours. The benzene is then removed at reduced pressure and the residue is added to 30 ml of distilled water. The pH of this aqueous mixture is adjusted to 6 by 0.1N aqueous hydrochloric acid. This mixture is extracted with 150 ml ethyl acetate. The separated organic extract is evaporated to yield an oil which crystallizes on trituration. Recrystallization from ethanol give 0.7 g of the subject compound as bright yellow fibrous crystals, m.p. 116°–117° C.

The thiourea of this invention should be orally administered in a daily amount of about 5 to 25 mg per kg. One or two daily doses are generally sufficient. Treatment up to 5 days is generally sufficient to cure the infection. At lower dosage levels a 2-day treatment is more effective if the second dose is given on nonconsecutive days, e.g. four days after the first dose.

The following biological studies evidence the efficacy of N-carbomethoxy-N'-methyl-N'-(2-nitro-4-n-propyloxyphenyl)thiourea as an oxyuricide. While the troublesome pinworm, species in man is Enterobius vermicularis, it is generally recognized in the art that efficacy against such pinworms can be reasonably measured in laboratory animals in terms of efficacy against the species Syphacia obvatata in mice. See, for example, Wagner, Laboratory Animal Care, Vol. 20, No. 1, 1970, pgs. 39–44 and references cited therein.

Male mice weighing 18–20 grams and naturally infected with S. obvatata were obtained from Flow Labs., Rockville, Maryland. Mice were given by gavage the drug either once or twice a day as indicated. After this therapy, the mice were fasted overnight and sacrificed. The ceca are removed and minced in 0.85% sodium chloride in petri dishes, and these were examined microscopically for the presence of worms. A standard biological suspension vehicle was used, each milliliter of which was composed of methylcellulose (15 cps) -4 mg, benzyl alcohol-9 mg, sodium chloride-9 mg, Polysorbate 80-5 mg and distilled water (q.s.). Pyrantal pamoate was used as a reference in some tests.

The activity of N-carbomethoxy-N'-methyl-N'-(2-nitro-4-n-propyloxyphenyl)thiourea and pyrantal pamoate against pinworms in mice is shown in Table 1. Single oral daily doses of up to 12 mg/kg/day given on consecutive days cured mice of pinworm. Levels of 10 mg/kg/day as single daily oral doses given twice, four days apart, also cured mice, and the drug was still very effective at 5 mg/kg/day.

The column "Significant Reduction" denotes whether or not, on the basis of standard statistical analysis of the data, the difference in pinworm count from that of the control group in the respective therapeutic regimen is statistically significant.

TABLE I

| Oral Dosing | | | | N-Carbomethoxy-N'-Methyl-N'-(2-Nitro-4-n-Propyloxyphenyl) Thiourea | | | Pyrantal Pamoate | | |
|---|---|---|---|---|---|---|---|---|---|
| Mg/Kg/ Day | No. Days | Doses/ Day | No. of Mice | % Infested | Mean Worm Burden | Significant Reduction | % Infested | Mean Worm Burden | Significant Reduction |
| 25 | 1 | 2 | 7 | 0 | 0 | yes | 43 | 0.6 | no |
| 25 | 2 | 1 | 7 | 0 | 0 | yes | | | |
| 12 | 3 | 1 | 7 | 0 | 0 | yes | | | |
| 10 | 2^A | 1 | 14 | 0 | 0 | yes | 43 | 2.0 | no |
| 10 | 2 | 1 | 7 | 0 | 0.1 | yes | 43 | 1.7 | no |
| 10 | 1 | 2 | 7 | 14 | 0.9 | yes | 43 | 3.1 | no |
| 5 | 2^A | 1 | 7 | 14 | 0.1 | yes | 29 | 0.6 | no |
| Pooled Controls | | | 40 | 73 | 4.0 | | | | |

^A- Treatment four (4) days apart

The thiourea of this invention can be administered in the usual oral dosage forms, e.g. tablets and capsules, containing standard pharmaceutical excipients. The thiourea can also be admixed with feed. Two exemplary formulations follow.

Tablets

-continued

|  | Gram Per 1,000 tablets |  |
|---|---|---|
| N-carbomethoxy-4'-methyl-N'-(2-nitro-4-propyl-oxyphenyl)thiourea | 50 | g |
| Lactose | 80 | g |
| Dicalcium phosphate, hydrous | 75 | g |
| Polyvinylpyrrolidone | 15 | g |
| Polyethylenglycol 1500 | 2.5 | g |
| Corn starch | 25 | g |
| Magnesium stearate | 2.5 | g |
|  | 250 | g |

Capsules

-continued

|  | Gram Per 1,000 capsules |  |
|---|---|---|
| N-carbomethoxy-N'-methyl-N'-(2-nitro-4-propyloxyphenyl)thiourea | 50 | g |
| Lactose | 148 | g |
| Magnesium stearate | 2 | g |
|  | 200 | g |

I claim:
1. A method of treating oxyuriasis comprising orally administering to an animal infected with pinworms 5 to 25 mg per kg per day of N-carbomethoxy-N'-methyl-N'-(2-nitro-4-n-propyloxyphenyl)thiourea.

* * * * *